United States Patent [19]

Milner et al.

[11] Patent Number: 6,013,811

[45] Date of Patent: Jan. 11, 2000

[54] PREPARATION PROCESS OF BENZODIFURANONE DYES

[75] Inventors: David John Milner, Whitefield; David Philip Devonald, Oldham, both of United Kingdom

[73] Assignee: BASF Aktiengesellschaft, Ludwigshafen, Germany

[21] Appl. No.: 09/117,179

[22] PCT Filed: Jan. 17, 1997

[86] PCT No.: PCT/GB97/00161

§ 371 Date: Dec. 30, 1998

§ 102(e) Date: Dec. 30, 1998

[87] PCT Pub. No.: WO97/28221

PCT Pub. Date: Aug. 7, 1997

[30] Foreign Application Priority Data

Feb. 1, 1996 [GB] United Kingdom .................. 9602046

[51] Int. Cl.$^7$ ...................... C07D 407/14; C07D 409/00; C07C 229/00

[52] U.S. Cl. ............................. 549/299; 549/60; 548/202; 548/204; 548/206; 548/214; 546/284.4; 546/341; 562/441

[58] Field of Search ...................... 549/299, 60; 562/441; 546/284.4, 341; 548/202, 204, 206, 214

Primary Examiner—Amelia Owens
Attorney, Agent, or Firm—Oblon, Spivak, McClelland, Maier & Neustadt, P.C.

[57] ABSTRACT

A process for the preparation of a polycyclic dye of Formula (1) which comprises steps: i) reaction of a compound of formula (2) with a compound of formula (3) or a derivative thereof to form an intermediate of formula (4) and ii) reaction of the intermediate of formula (4) with an aromatic compound of formula (5): B—H optionally in the presence of an oxidizing agent, wherein: A and B each independently is optionally substituted aryl; and $X^1$ and $X^2$ each independently is —H, halo, alkyl, or alkoxy.

12 Claims, No Drawings

PREPARATION PROCESS OF BENZODIFURANONE DYES

The present invention relates to a process for the preparation of polycyclic dyes, particularly benzodifuranone dyes, to trihydroxydicarboxylic acids and to a process for their preparation.

According to the present invention, there is provided a process for the preparation of a polycyclic dye of Formula (1):

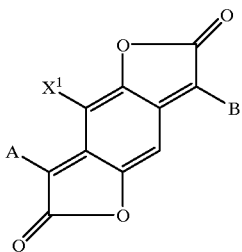

which comprises the steps:
  i) reaction of a compound of Formula (2):

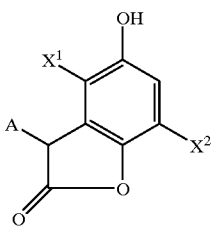

with a compound of Formula (3):

or a derivative thereof to form an intermediate of Formula (4):

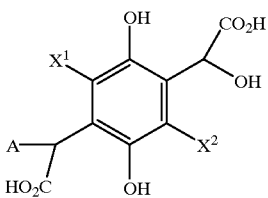

and
  ii) reaction of the intermediate of Formula (4) with an aromatic compound of Formula (5):

    Formula (5)

optionally in the presence of an oxidising agent, wherein:
A and B each independently is optionally substituted aryl; and
$X^1$ and $X^2$ each independently is —H, halo, alkyl or alkoxy.

A and B each independently is preferably optionally substituted phenyl or naphthyl but may also be an optionally substituted heterocyclic aromatic radical such as pyridyl, thienyl, thiazolyl or isothiazolyl.

Where $X^1$ or $X^2$ is halo it is preferably —F, —Cl or —Br. Where $X^1$ or $X^2$ is alkyl it is preferably straight or branched chain $C_{1-6}$-alkyl. Where $X^1$ or $X^2$ is alkoxy, it is preferably straight or branched chain $C_{1-6}$-alkoxy. $X^1$ and $X^2$ are preferably —H.

Where A and B are substituted the optional substituents may be selected from alkyl; alkenyl; alkoxy; alkoxyalkyl; alkoxyalkoxy; alkylcarbonyl; alkoxycarbonyl; alkoxycarbonylalkoxy; alkoxyalkoxycarbonylalkoxy; cyanoalkyl; cyanoalkoxy; hydroxyalkyl; hydroxyalkoxy; haloalkyl, especially fluoro-, chloro- or bromoalkyl; haloalkoxy, especially fluoro-, chloro- or bromoalkoxy; alkythio; arylthio; aryloxy; alkylsulphonyl; arylsulphonyl; halo, especially chloro or bromo; hydroxy; cyano; nitro; amino; alkylamino; dialkylamino; cycloalkylamino; alkylcarbonylamino; arylcarbonylamino; alkylsulphonylamino; arylsulphonylamino; cycloalkyl; and alkylamino and dialkylamino substituted by —CN, —Cl, —F, —Br, —OH, —$COOC_{1-4}$-alkyl, —$COOC_{1-4}$-alkyl$OC_{1-4}$-alkyl, -phenyl, —$OCOC_{1-4}$-alkyl; and preferably such groups in which the alkyl or alkoxy contains from 1 to 8 carbon atoms, especially from 1 to 4 carbon atoms; the alkenyl contains from 2 to 6 carbon atoms, especially from 2 to 4 carbon atoms; the aryl is phenyl or naphthyl and the cycloalkyl contains from 3 to 8 carbon atoms, more preferably from 4 to 6 carbon atoms and especially 6 carbon atoms. Each alkyl, alkoxy or alkenyl may be straight or branched chain alkyl, alkoxy or alkenyl respectively.

Where A or B is phenyl it is preferably unsubstituted or substituted by from 1 to 5, more preferably by from 1 to 3 of the optional substituents described above. Where A or B is phenyl and one substituent group is present, this is more preferably in the 4-position. Where 2 substituent groups are present, they are preferably in the 3- and 4-positions and where 3 substituent groups are present, they are preferably in the 3-, 4- and 5-positions.

The optional substituents for A and B are preferably selected from $C_{1-4}$-alkyl, $C_{1-4}$-alkoxy, hydroxy, $C_{1-4}$-alkoxy-$C_{1-4}$-alkoxycarbonyl$C_{1-4}$-alkoxy, amino, $C_{1-4}$-alkylamino and $(C_{1-4}$-alkyl$)_2$amino and combinations thereof.

Suitable derivatives of compounds of Formula (3) include compounds in which the aldehyde group and/or the acid group are protected, preferably oxime, nitrile, —$CCl_3$ and ester derivatives.

The first step of the process may be carried out in a liquid medium. Suitable liquid media include water, alkanols, such as methanol, ethanol or propanol, dimethyl formamide and tetrahydrofuran or combinations thereof. The liquid medium preferably contains a base. Suitable bases may be inorganic or organic and include alkali metal hydroxides such as sodium or potassium hydroxide, alkali metal carbonates and bicarbonates, such as sodium or potassium bicarbonate and sodium or potassium hydrogen carbonates, nitrogen containing bases such as mono-, di and tri-alkylamines, pyrrolidines and metal hydrides such as sodium hydride.

The liquid medium is preferably water, water/alkanol, such as water/methanol which contains an alkali metal hydroxide such as sodium or potassium hydroxide, more preferably water/methanol containing sodium hydroxide. The first step of the process may be carried out at a temperature of from −20° to 80° C., preferably at a temperature from −10° C. to 25° C., more preferably at a temperature of from −5° C. to 15° C. and especially at from 0° C. to 10° C.

The intermediate of Formula (4) may be isolated by any convenient means such as neutralisation of the reaction mixture with an acid, preferably a mineral acid such as hydrochloric acid, removing any organic liquid media by evaporation, optionally under vacuum to leave a residue which may be freeze dried, or by extraction from the reaction mixture with an organic liquid, for example an ester such as ethyl acetate.

The second step of the process may be carried out in a liquid medium. Suitable liquid media include nitroaromatics such as nitrobenzene, aromatic hydrocarbons such as benzene and toluene, and chloroaromatics such as chlorobenzene and dichlorobenzene.

An acid catalyst is preferably added to the reaction mixture. Suitable acid catalysts include alkyl or aryl sulphonic acids such as methanesulphonic acid, p-toluenesulphonic acid, p-dodecylbenzenesulphonic acid, alkanoic acids such as acetic and propionic acids, and inorganic acids such as sulphuric and hydrochloric acids.

An oxidising agent is preferably used and this may be present throughout or added at the end of the second step of the process. Suitable oxidising agents include aromatic nitro compounds such as nitrobenzene, benzoquinone or its derivatives such as chloranil and bromanil, peroxides such as hydrogen peroxide, persulphates such as sodium persulphate and oxygen.

The second step of the process may be carried out at a temperature of from 20° C. to 200° C., preferably at from 100° C. to 180° C. and especially at from 120° C. to 160° C.

The product may be isolated by any convenient means such as by adding an aliphatic hydrocarbon such as hexane to the reaction mixture and collecting the precipitated product by filtration.

The compound of Formula (2) may be prepared as described in GB 2068402A by reaction of hydroquinone or dihydroxybenzene with an optionally substituted mandelic acid at an elevated temperature in the presence of an acid catalyst followed by pouring the reaction mixture into water and collecting the precipitated product by filtration.

The compounds of Formula (4) are novel and accordingly form a further feature of the present invention. The process for the preparation of compounds of Formula (4) using the first step of the process described above forms a further feature of the present invention.

According to a further feature of the present invention, there is provided a process for the preparation of a compound of Formula (6):

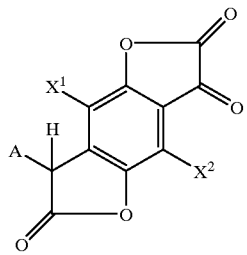

in which a compound of Formula (4) is oxidised where A, $X^1$ and $X^2$ are as hereinbefore defined.

The process may be performed in a liquid medium such as 1,2-dichlorobenzene at a temperature of from 80° C. to 200° C. The compound of Formula (6) may be isolated from the reaction mixture by any convenient means such as cooling the reaction mixture and collecting the product by filtration.

The invention is further illustrated by the following examples:

EXAMPLE 1

Preparation of 3-phenyl-7-(4-hydroxyphenyl)-2,6-dioxo-2,6-dihydrobenzo-[1:2-b,4:5-b ]-difuran i) Preparation of

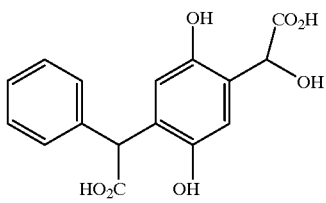

5-hydroxy-2-oxo-3-phenyl-2,3-dihydrobenzofuran (2:26 parts) and sodium hydroxide (0.4 parts) were dissolved in methanol (5 parts) and cooled to 5° C. 50% Aqueous glyoxylic acid (1.48 parts) and sodium hydroxide (0.4 parts) in water (3 parts) were added dropwise at approximately equal rates over 30 minutes. The reaction mixture was neutralised by adding hydrochloric acid (32%) and the methanol was removed under vacuum to leave a residue which was freeze dried.

Analysis by mass spectrometry (FAB) gave an ion m/e 317 consistent with the above structure.

ii) The residue (0.82 parts) from i) above, phenol (0.5 parts) and p-toluenesulphonic acid (4 parts) in nitrobenzene (20 parts) were heated at 140° C. overnight. The reaction mixture was cooled and petroleum ether added to precipitate a solid which was collected by filtration. The solid had λmax=512 nm, m/e 356 and co-eluted on silica using 9:1 ethanol:methanol as eluent, with an authentic sample of 3-phenyl-7-(4-hydroxyphenyl)-2,6-dioxo-2,6-dihydrobenzo-[1:2-b,4:5-b']-difuran.

EXAMPLE 2

Preparation of 3-phenyl-7-(4-methoxyphenyl)-2,6-dioxo-2,6-dihydrobenzo-[1:2b,4:5-b']-difuran i) The procedure of Example 1 i) was followed except that the product was isolated by extraction with ethyl acetate.

ii) The residue (3.55 parts) from i), anisole (40 parts) and p-toluenesulphonic acid (10 parts) were heated at 140° C. for 2 days before cooling to 80° C. and adding chloranil (2 parts). The reaction mixture was heated at 130° C. for 3 hours before cooling to ambient temperature and adding hexane to precipitate a solid. The solid was collected by filtration. The solid had λmax=498 nm, m/e 370 and co-eluted on silica with an authentic sample of 3-phenyl-7-(4-methoxyphenyl)-2,6-dioxo-2,6-dihydrobenzo-[1:2-b,4:5-b']-difuran.

We claim:

1. A process for the preparation of a polycyclic dye of Formula (1):

Formula (1)

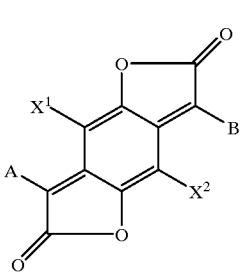

which comprises the steps:

i) reaction of a compound of Formula (2):

Formula (2)

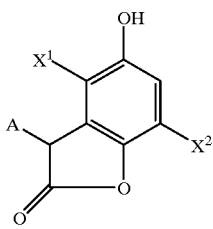

with a compound of Formula (3):

Formula (3)

CHO
|
CO$_2$H or a derivative thereof to form an intermediate of Formula (4):

Formula (4)

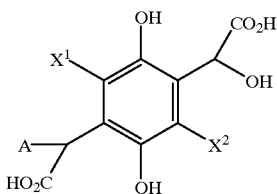

and ii) reaction of the intermediate of Formula (4) with an aromatic compound of Formula (5):

B—H  Formula (5)

optionally in the presence of an oxidising agent, wherein:

A and B each independently is optionally substituted aryl or heterocyclic aromatic radical; and $X^1$ and $X^2$ each independently is —H, halo, alkyl or alkoxy.

2. A compound of Formula (4):

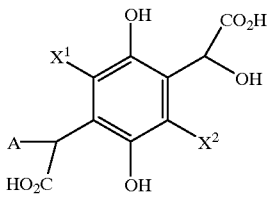

in which

A is optionally substituted aryl or heterocyclic aromatic radical; and $X^1$ and $X^2$ each independently is —H, halo, alkyl or alkoxy.

3. A process for the preparation of a compound of Formula (6):

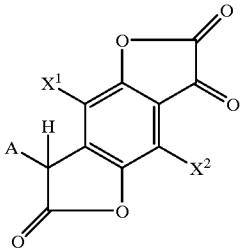

in which a compound of Formula (4) is oxidised, wherein:

A is optionally substituted aryl or heterocyclic aromatic radical; and $X^1$ and $X^2$ each independently is —H, halo, alkyl or alkoxy.

4. A process according to claim 1, wherein A and B each independently is an optionally substituted phenyl, naphthyl, pyridyl, thienyl, thiazolyl or isothiazolyl.

5. A process according to claim 1, wherein step (i) is conducted in a liquid medium at a temperature of −10° C. to 80° C. and step (ii) is conducted in a liquid medium at a temperature of 20° C. to 200° C. optionally in the presence of an acid catalyst.

6. A process according to claim 5, wherein step (ii) is conducted in the presence of an oxidizing agent selected from an aromatic nitro compound, a benzoquinone, a peroxide, a persulphate or oxygen.

7. A compound according to claim 2, wherein A is an optionally substituted phenyl, naphthyl, pyridyl, thienyl, thiazolyl, or isothiazolyl.

8. A compound according to claim 7, wherein $X^1$ and $X^2$ are each H and A is phenyl.

9. A process according to claim 3, wherein A is an optionally substituted phenyl, naphthyl, pyridyl, thienyl, thiazolyl or isothiazolyl.

10. A process according to claim 3, wherein the oxidising step is conducted in a liquid medium at a temperature of 80° C. to 200° C.

11. A process for the preparation of a compound of Formula (4) which comprises reacting a compound of Formula (2) with a compound of Formula (3) in a liquid medium at a temperature of −10° C. to 80° C.

12. A process as in claim 11, wherein the reaction is conducted at a temperature of −10° C. to 25° C. and the liquid medium is water or a water/alkanol mixture optionally containing an alkali metal hydroxide.

* * * * *